US00PP13940P29

(12) United States Plant Patent
Trees

(10) Patent No.: US PP13,940 P2
(45) Date of Patent: Jul. 8, 2003

(54) GERANIUM PLANT NAMED 'BALDESCART'

(75) Inventor: Scott C. Trees, Shell Beach, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/114,879

(22) Filed: Apr. 1, 2002

(51) Int. Cl.[7] ..... A01H 5/00
(52) U.S. Cl. ..... Plt./330
(58) Field of Search ..... Plt./330

*Primary Examiner*—Kent Bell
(74) *Attorney, Agent, or Firm*—C. A. Whealy

(57) ABSTRACT

A new and distinct cultivar of Geranium plant named 'Baldescart', characterized by its upright and mounded growth habit; freely basal branching habit; medium green-colored leaves with a distinct zonation pattern; and scarlet red-colored semi-double flowers.

2 Drawing Sheets

BOTANICAL CLASSIFICATION/CULTIVAR DESIGNATION

*Pelargonium×hortorum* cultivar 'Baldescart'.

BACKGROUND OF THE INVENTION

The present invention relates to a new and distinct cultivar of Geranium plant, botanically known as *Pelargonium×hortorum*, and hereinafter referred to by the name 'Baldescart'.

The new Geranium is a product of a planned breeding program conducted by the Inventor in Arroyo Grande, Calif. The objective of the breeding program is to develop new vigorous Zonal Geranium cultivars that flower uniformly and have attractive flower and foliage colors.

The new Geranium originated from a cross-pollination made by the Inventor in 1998 of a proprietary *Pelargonium×hortorum* selection identified as code number 7788-35, not patented, as the female, or seed, parent with a proprietary *Pelargonium×hortorum* selection identified as code number 8120-24, not patented, as the male, or pollen, parent. The cultivar Baldescart was discovered and selected by the Inventor as a flowering plant within the progeny from this cross-pollination in a controlled environment in Arroyo Grande, Calif.

Asexual reproduction of the new cultivar by terminal cuttings taken at Arroyo Grande, Calif., since June, 2000 has shown that the unique features of this new Geranium are stable and reproduced true to type in successive generations of asexual reproduction.

SUMMARY OF THE INVENTION

The following traits have been repeatedly observed and are determined to be the unique characteristics of 'Baldescart'. These characteristics in combination distinguish 'Baldescart' as a new and distinct Geranium cultivar:

1. Upright and mounded growth habit.
2. Freely basal branching habit.
3. Medium green-colored leaves with a distinct zonation pattern.
4. Scarlet red-colored semi-double flowers.

Plants of the new Geranium differ primarily from plants of the female parent selection in flower form and leaf zonation. Plants of the new Geranium differ primarily from plants of the male parent selection in leaf zonation.

The new Geranium can be compared to the cultivar, 'Fisboogy', disclosed in U.S. Plant Pat. No. 9,774. However, in side-by-side comparisons conducted in West Chicago, Ill., plants of the new Geranium differed from plants of the cultivar Fisboogy in the following characteristics:

1. Plants of the new Geranium had larger and lighter green-colored leaves than plants of the cultivar Fisboogy.
2. Plants of the new Geranium flowered about two weeks earlier than plants of the cultivar Fisboogy.
3. Plants of the new Geranium had fewer flowers per umbel than plants of the cultivar Fisboogy.
4. Plants of the new Geranium had longer peduncles than plants of the cultivar Fisboogy.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical flowering plant of 'Baldescart'.

The photograph on the second sheet is a close-up view of a typical leaf and flower of 'Baldescart'. Flower and foliage colors in the photographs may differ slightly from the color values cited in the detailed botanical description which accurately describe the colors of the new Geranium.

DETAILED BOTANICAL DESCRIPTION

The cultivar Baldescart has not been observed under all possible environmental conditions. The phenotype may vary somewhat with variations in environment such as temperature and light intensity, without, however, any variance in genotype. The aforementioned photograph and following observations and measurements describe plants grown in West Chicago, Ill., under commercial practice in a polycarbonate-covered greenhouse with day temperatures about 20 to 22° C., night temperatures about 18 to 20° C. and light levels about 5,000 to 7,500 foot-candles. Plants used for the photograph and description were about 11 to 13 weeks from planting rooted cuttings. In the following description, color references are made to The Royal Horticultural Society Colour Chart, 1995 Edition, except where general terms of ordinary dictionary significance are used.

Botanical classification: *Pelargonium×hortorum* cultivar Baldescart.

Parentage:

*Female parent.*—Proprietary *Pelargonium×hortorum* selection identified as code number 7788-35, not patented.

*Male parent.*—Proprietary *Pelargonium×hortorum* selection identified as code number 8120-24, not patented.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Upright and mounded growth habit. Appropriate for 10-cm and larger containers.

*Growth and branching habit.*—Vigorous and freely basal branching with about three lateral branches at the base. Pinching, that is, removal of terminal apices, is typically not required.

*Plant height* (*to top of foliage*).—About 12.4 cm.

*Plant width.*—About 17.5 cm.

*Lateral branches.*—Length: About 7 cm. Internode length: About 9 mm. Texture: Pubescent. Color: 144C.

*Foliage description: Arrangement: Opposite, simple. Quantity of leaves per lateral branch: About* 14. Length: About 5.1 cm. Width: About 8.5 cm. Shape: Reniform. Apex: Rounded. Base: Cordate. Margin: Crenate. Venation: Palmate. Texture, upper and lower surfaces: Velvety; pubescent. Color: Young and fully expanded foliage, upper surface: 146A; zonation pattern, darker than 146A in color and located on the outer half of the leaf. Young and fully expanded foliage, lower surface: 146C. Venation, upper and lower surfaces: 144B. Petiole: Length: About 7 cm. Diameter: About 2 mm. Texture, upper and lower surfaces: Pubescent. Color, upper and lower surfaces: 146A.

Flower description:

*Flower arrangement and type.*—Single flowers arranged in hemispherical umbels arising from apical leaf axils. Umbels displayed above the foliage. At full flowering, usually about six open umbels and about four developing umbels per plant. Flowers semi-double and rounded in shape. Umbels persistent. Flowers not fragrant.

*Flowering season.*—Year-round under greenhouse conditions. In the garden, flowering is continuous from spring until fall. Plants start flowering about nine weeks after planting.

*Flower longevity.*—Flowers last about ten days on the plant.

*Umbels.*—Diameter: About 7.2 cm. Height: About 4.4 cm. Number of flowers per umbel: About 12. Flower diameter: About 4.4 cm. Flower depth (height): About 1.7 cm.

*Flower buds.*—Length: About 1.5 cm. Diameter: About 7 mm. Shape: Ovoid. Color: 45B.

*Petals/petaloids.*—Quantity: About seven petals and about one to five petaloids per flower. Petaloids variable in size and shape. Arrangement: Imbricate. Petal length: Upper petals: About 2.5 cm. Lower petals: About 2.3 cm. Petal width: Upper petals: About 1.9 cm. Lower petals: About 2 cm. Petal shape: Obovate. Petal/petaloid apex: Rounded, obtuse. Petal/petaloid base: Attenuate. Petal/petaloid margin: Entire. Petal/petaloid texture, upper and lower surfaces: Smooth. Petal/petaloid aspect: Slightly cupped. Petal/petaloid color: When opening and fully opened, upper surface: 43A; color becoming closer to 45C with subsequent development; venation, 43A. When opening and fully opened, lower surface: 44B; venation, 44B.

*Sepals.*—Quantity: Five per flower; not imbricate on open flowers. Length: About 1.1 cm. Width: About 3 mm. Shape: Ensiform to lanceolate. Apex: Acuminate. Margin: Entire. Texture, upper surface: Glabrous. Texture, lower surface: Pilose. Color, upper surface: 144A overlain with 183B, most prominent towards the base. Color, lower surface: 144A.

*Peduncle* (*umbel stem*).—Length: About 13.5 cm. Angle: Erect. Strength: Strong. Texture: Pubescent. Color: 144A.

*Pedicel* (*individual flower stem*).—Length: About 2.4 cm. Angle: Erect. Strength: Strong. Texture: Pubescent. Color: 144C overlain with 181A.

*Reproductive organs.*—Androecium: Anther quantity: Five per flower. Anther length: About 2.5 mm. Anther color: Lighter than 64D. Pollen amount: Moderate. Pollen color: 170A. Gynoecium: Pistil quantity: One per flower. Pistil length: About 7 mm. Stigma shape: Five-parted, star-shaped. Stigma color: 46C. Style length: About 2 mm. Style color: 46C.

*Seed/fruit.*—None observed.

Disease/pest resistance: Resistance to pathogens and pests common to Pelargonium has not been observed.

It is claimed:

1. A new and distinct cultivar of Geranium plant named 'Baldescart', as herein illustrated and described.

* * * * *

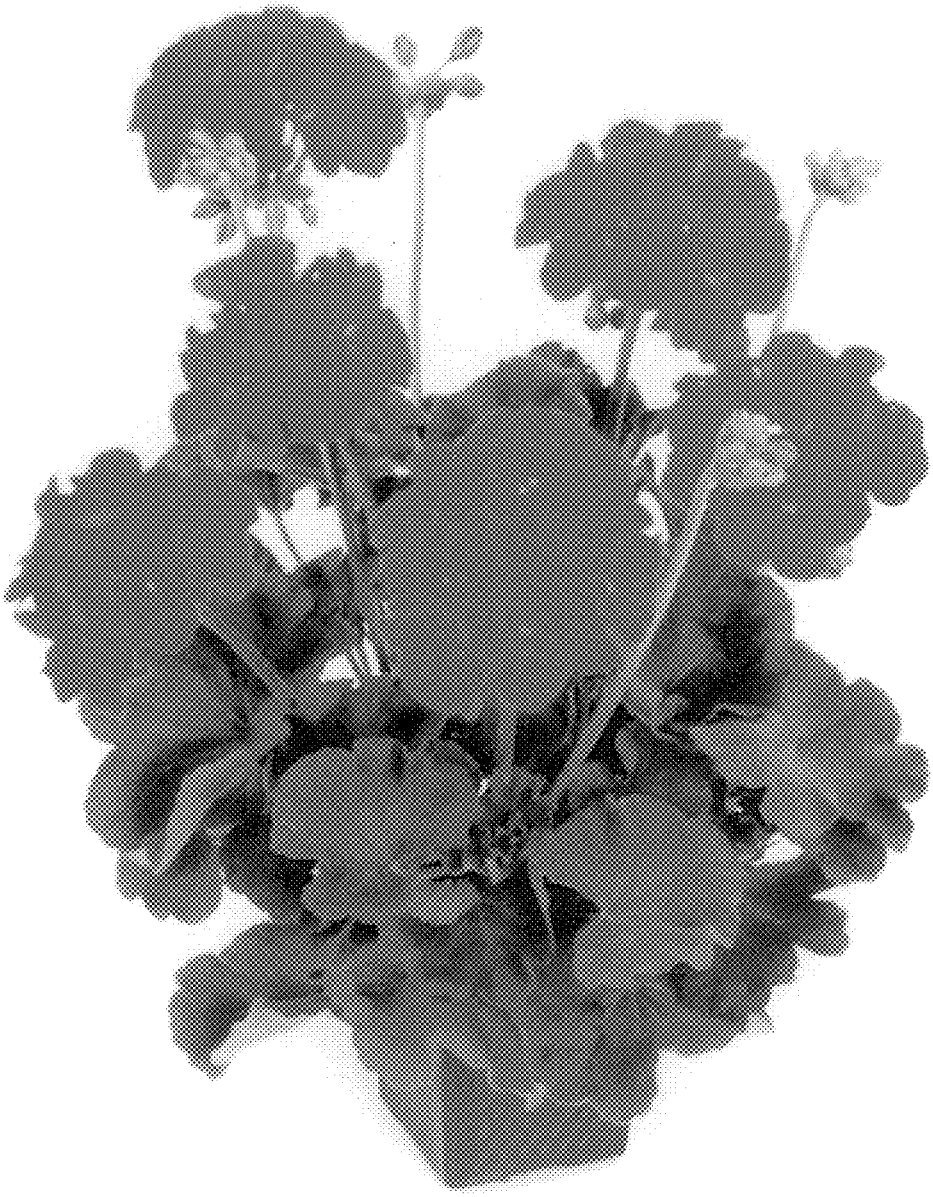

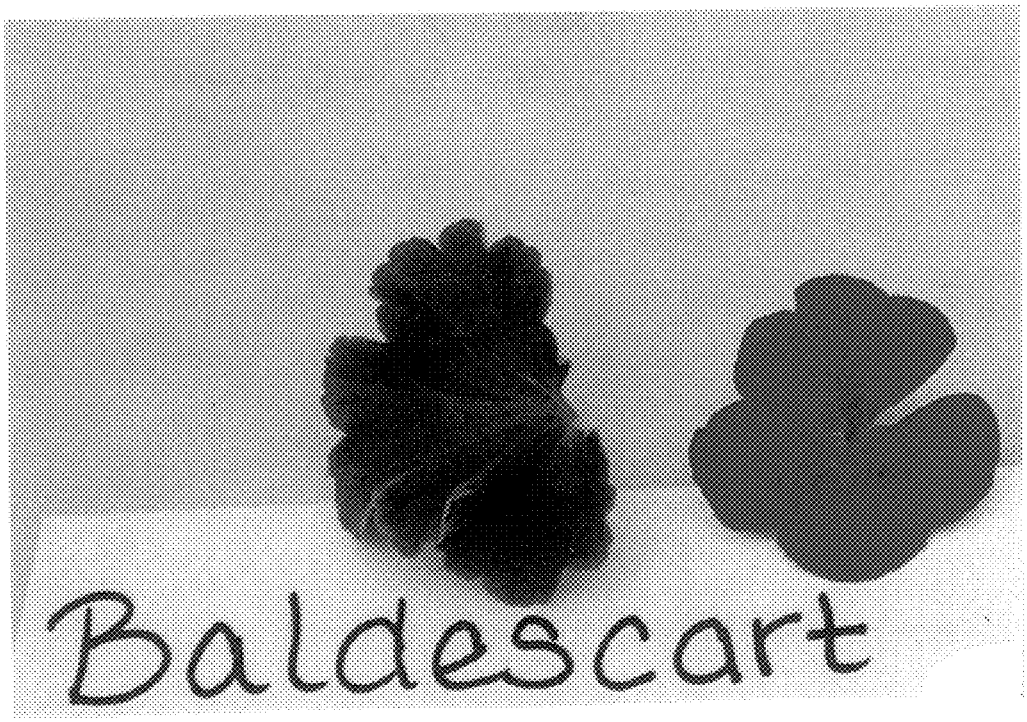
Baldescart